(12) United States Patent
Shibuya et al.

(10) Patent No.: US 9,297,753 B2
(45) Date of Patent: Mar. 29, 2016

(54) PHOTOELECTRIC SMOKE SENSOR

(75) Inventors: Tadayuki Shibuya, Tokyo (JP); Takuya Ookawa, Tokyo (JP); Masao Iguchi, Tokyo (JP)

(73) Assignee: FENWAL CONTROLS OF JAPAN, LTD., Tokyo (JP)

( * ) Notice: Subject to any disclaimer, the term of this patent is extended or adjusted under 35 U.S.C. 154(b) by 56 days.

(21) Appl. No.: 14/238,052

(22) PCT Filed: Aug. 29, 2011

(86) PCT No.: PCT/JP2011/069438
§ 371 (c)(1),
(2), (4) Date: Apr. 21, 2014

(87) PCT Pub. No.: WO2013/030918
PCT Pub. Date: Mar. 7, 2013

(65) Prior Publication Data
US 2015/0146204 A1    May 28, 2015

(51) Int. Cl.
*G01N 21/01* (2006.01)
*G01N 21/53* (2006.01)
(Continued)

(52) U.S. Cl.
CPC ............... *G01N 21/53* (2013.01); *G01N 21/01* (2013.01); *G08B 17/107* (2013.01); *G01N 15/0205* (2013.01); *G01N 21/4738* (2013.01); *G08B 17/10* (2013.01); *G08B 17/103* (2013.01)

(58) Field of Classification Search
CPC ... G01N 21/01; G01N 21/53; G01N 21/0205; G01N 21/4738; G08B 17/10; G08B 17/103; G08B 17/107; G08B 29/043; G08B 29/145
USPC .................................................. 356/335–344
See application file for complete search history.

(56) References Cited

U.S. PATENT DOCUMENTS 3,431,423 A * 3/1969 Keller ........................... 250/574
3,863,076 A * 1/1975 Steele .................. G08B 17/107
  250/239

(Continued)

FOREIGN PATENT DOCUMENTS

CN    201000431    1/2008
JP    H03-296897 B2    12/1991
(Continued)

OTHER PUBLICATIONS

Office Action Dated May 18, 2015 Issued in Corresponding Russian Patent Application No. 2014101493.
(Continued)

*Primary Examiner* — Tri Ton
*Assistant Examiner* — Jarreas C Underwood
(74) *Attorney, Agent, or Firm* — Bacon & Thomas, PLLC

(57) ABSTRACT

A photoelectric smoke sensor capable of detecting smoke with high accuracy is provided.
The present invention relates to the photoelectric smoke sensor which detects smoke flowing into a housing by light. The present invention is provided with a light emitting element provided by being faced with a detection region in the housing and emitting inspection light to the detection region, a light receiving element provided at a position shifted from an optical path of the inspection light of the light emitting element by being faced with the detection region and receiving diffused light which is the inspection light having hit the smoke and diffused, so as to detect the smoke, and a reflecting member provided in the housing and deflecting and reflecting the inspection light emitted from the light emitting element so as not to enter the light receiving element.

6 Claims, 9 Drawing Sheets

(51) Int. Cl.
   *G08B 17/107*   (2006.01)
   *G01N 21/47*    (2006.01)
   *G08B 17/103*   (2006.01)
   *G08B 17/10*    (2006.01)
   *G01N 15/02*    (2006.01)

(56) References Cited

U.S. PATENT DOCUMENTS

| | | | | |
|---|---|---|---|---|
| 4,226,533 | A * | 10/1980 | Snowman | 356/338 |
| 5,138,302 | A * | 8/1992 | Nagaoka | G08B 17/107 250/574 |
| 5,231,378 | A * | 7/1993 | Dennis | G08B 17/107 250/574 |
| 5,581,241 | A * | 12/1996 | Kaufman et al. | 340/630 |
| 5,587,790 | A * | 12/1996 | Nagashima | G08B 17/107 250/574 |
| 5,642,099 | A * | 6/1997 | Nagashima | G08B 17/107 250/574 |
| 6,756,905 | B2 * | 6/2004 | Rattman et al. | 340/630 |
| 7,084,432 | B2 * | 8/2006 | Kachi et al. | 257/81 |
| 7,238,967 | B2 * | 7/2007 | Kuwabara et al. | 257/98 |
| 7,429,757 | B2 * | 9/2008 | Oyama | H01L 33/62 257/79 |
| 7,697,140 | B2 * | 4/2010 | Iguchi | G08B 17/107 250/574 |
| 7,948,627 | B2 * | 5/2011 | Iguchi | G08B 17/107 250/574 |
| 2009/0021729 | A1 | 1/2009 | Iguchi et al. | |

FOREIGN PATENT DOCUMENTS

| | | |
|---|---|---|
| JP | H04-5797 A | 1/1992 |
| JP | 07182574 | 7/1995 |
| JP | 08263767 | 10/1996 |
| JP | 2004-220155 | 8/2004 |
| JP | 2005-309735 A | 11/2005 |
| JP | 2008-287452 | 11/2008 |
| JP | 2009-003510 | 1/2009 |
| JP | 2009-229414 | 10/2009 |
| RU | 99641 U1 | 11/2010 |
| WO | WO2006/112085 A1 | 10/2006 |

OTHER PUBLICATIONS

ISR Issued in European Patent Application No. 11871783.4 on May 6, 2015.

* cited by examiner

FIG.9

| ITEM | EXISTING PRODUCT | HIGH SENSITIVITY PRODUCT WITH AN EXISTING LED | HIGH SENSITIVITY PRODUCT WITH A NEW LED | |
|---|---|---|---|---|
| ADL | 108 | 13 | 25 | ADL DECREASED |
| ADH (5%/m) | 147 | 90 | 109 | SIGNAL INCREASED |
| ADH-ADL (5%/m) | 39 | 77 | 84 | AMOUNT OF CHANGE INCREASED |
| S/N RATIO | 0.37 | 5.93 | 3.3 | NOISE RESISTANCE IMPROVED |
| AMOUNT OF CHANGE OF 1%/m | 7.8 | 15.4 | 17 | AMOUNT OF CHANGE INCREASED |

PHOTOELECTRIC SMOKE SENSOR

TECHNICAL FIELD

The present invention relates to a photoelectric smoke sensor using a light emitting element and a light receiving element.

BACKGROUND ART

The photoelectric smoke sensor is equipment for detecting smoke caused by an outbreak of a fire in a space. Specifically, the photoelectric smoke sensor detects smoke flowing into a housing of the photoelectric smoke sensor by light. Such a photoelectric smoke sensor is installed in an indoor space or a space in various types of devices, and detects smoke in the space.

Photoelectric smoke sensors installed in such space need to be small-sized. The present applicant has suggested a small-sized photoelectric smoke sensor in Patent Document 1. This will be roughly described on the basis of FIG. 1. In the description below, upper, lower, right and left sides are based on the state in FIG. 1.

A smoke sensor 1 is composed of a cylinder portion 2 and a flat box portion 3 extended upward from the cylinder portion 2.

The cylinder portion 2 has functions of allowing intrusion of smoke and guiding the smoke into the inside while preventing entry of ambient light into the inside of the smoke sensor 1. A mountain-shaped labyrinth 4 having a mountain shape (a conical shape with the head part cut off) is provided in a lower-surface opening of the cylinder portion 2. The mountain-shaped labyrinth 4 has its center part raised in a shape of a mountain and has a plurality of openings 5 functioning as an introduction port for the smoke and also preventing entry of the ambient light provided in the peripheral edge portion thereof.

The flat box portion 3 has a substantially rectangular solid shape and has a smoke detection function. A lateral width of the flat box portion 3 is the same as an outer diameter of the cylinder portion 2, and the flat box portion 3 extends upward from the cylinder portion 2 so that the center axis of its own matches the center axis of the cylinder portion 2.

In an upper part of the flat box portion 3, a side-face small hole 7 is provided. This side-face small hole 7 functions as an opening when the smoke is led out from the inside of the smoke sensor 1 to the outside. That is, the smoke introduced into the smoke sensor 1 through the opening 5 of the mountain-shaped labyrinth 4 and the side-face small hole (not shown) of the cylinder portion 2 is led out through the side-face small hole 7 of the flat box portion 3. The smoke might flow into the smoke sensor 1 also through the side-face small hole 7.

Inside of the smoke sensor 1, a light emitting element 8 and a light receiving element 9 are provided.

The light emitting element 8 is an element provided by being faced with a detection region AR in the housing of the flat box portion 3 and emitting inspection light to the detection region AR. The light emitting element 8 is provided at a position in an upper part of an internal space of the flat box portion 3 (upper left in FIG. 1) by a light emitting element accommodation portion 11. The light emitting element accommodation portion 11 accommodates the light emitting element 8 so that the inspection light emitted from the light emitting element 8 is emitted only forward. An optical window portion 12 is provided in front of the light emitting element accommodation portion 11.

The light receiving element 9 is provided at a position in the lower left in the internal space of the flat box portion 3 by a light receiving element accommodation portion 13. The light receiving element accommodation portion 13 accommodates the light receiving element 9 in a bottom portion thereof and has an objective lens 14 attached in an upper part thereof.

The light receiving element 9 is provided by being faced with the detection region AR at a position shifted from an optical path of the inspection light of the light emitting element 8 and receives diffused light which is the inspection light diffused by having hit the smoke and detects the smoke. Specifically, the optical axis of the light emitting element 8 and the optical axis of the light receiving element 9 are configured to cross each other at an angle of approximately 120 degrees, and the vicinity of the intersection becomes the smoke detection region AR. As a result, if there is smoke in the detection region AR, the inspection light from the light emitting element 8 is diffused by the smoke, the diffused light reaches the light receiving element 9, and the presence of the smoke is detected.

Between the light emitting element 8 and the light receiving element 9 (at a position left to the detection region AR), a shielding plate 15 is provided for preventing direct entry of the inspection light from the light emitting element 8 into the light receiving element 9 without being diffused.

In the right of the light receiving element accommodation portion 13, two labyrinth pieces 17 and 18 are provided. The labyrinth piece 17 is formed with inclination in an upper right direction and guides an air flow from the lower side to the upper right direction by its lower surface. Moreover, an end portion in the upper direction of the labyrinth piece 17 is bent to an upper left direction. This end portion has a function of leading the air flow raised along an upper face toward the detection region AR. The labyrinth piece 18 is formed with inclination in an upper left direction at a position upper left of the labyrinth piece 17. The labyrinth piece 18 guides the air flow directly from below and the air flow flowing along the inclination of a lower inclined surface 13a of the light receiving element accommodation portion 13 to the upper left direction. In the upper left direction of the labyrinth piece 18, an upper inclined surface 13b of the light receiving element accommodation portion 13 is provided. The air flow flowing toward the upper inclined surface 13b of the light receiving element accommodation portion 13 is directed to the direction of the detection region AR by the inclined surface 13b.

At a lower end position of the side-face small hole 7 of the flat box portion 3, a labyrinth piece 20 extending substantially to the left is provided. This labyrinth piece 20 is bent at the intermediate position thereof so as to be directed to the upper left direction. The air flow having passed the detection region AR and further rising is narrowed by an upper inclined surface 11a of the light emitting element accommodation portion 11 and the lower inclined surface of the labyrinth piece 20 and reaches the upper surface of the internal space. Then, it is directed toward the side-face small hole 7 by a pressure of the air flow after that and is led out of the side-face small hole 7. Reference numeral 21 denotes an insect screen. Moreover, a labyrinth piece 22 is provided below the labyrinth piece 17.

The above-described mountain-shaped labyrinth 4, the lower inclined surface 13a of the light receiving element accommodation portion 13, the labyrinth pieces 17, 18, 20, and 22 and the like suppress entry of the ambient light into the inside.

By means of the above configuration, the inspection light from the light emitting element 8 is emitted to the detection region AR. At this time, direct incidence of the inspection light into the light receiving element 9 is prevented by the shielding plate 15. The ambient light tries to intrude through the opening 5 of the mountain-shaped labyrinth or the side-face small hole 7, but this ambient light is prevented by the labyrinth pieces 17, 18, 20, and 22 and the like.

If smoke intrudes through the opening 5 of the mountain-shaped labyrinth or the side-face small hole 7 in this state, the smoke intrudes into the detection region AR through the labyrinth pieces 17, 18, 20, and 22 and the like. Then, the presence of the smoke is detected when the inspection light from the light emitting element 8 is diffused by the smoke, and the diffused light reaches the light receiving element 9. Patent Document: International Publication No. WO2006-112085

DISCLOSURE OF THE INVENTION

Problems to be Solved by the Invention

By means of the above-described prior-art photoelectric smoke sensor, smoke caused by a fire can be detected, but if concentration of the smoke is low, detection becomes difficult. That is, if the smoke intrudes the detection region AR, the inspection light from the light emitting element 8 is diffused by the smoke, the diffused light reaches the light receiving element 9, and the presence of the smoke is detected, but if the concentration of the smoke is low, a diffused amount of the inspection light becomes small, and detection becomes difficult.

Thus, a photoelectric smoke sensor which can sense smoke with higher accuracy than the prior-art photoelectric smoke sensor is in demand.

The present invention was made in view of the above-described circumstances, and a photoelectric smoke sensor which is small-sized and is capable of detecting smoke with higher accuracy is provided.

Means to Solve the Problems

In order to solve the above-described problems, a photoelectric smoke sensor detecting smoke flowing into a housing by light, according to the present invention, is provided with a light emitting element provided by being faced with a detection region in the housing and emitting inspection light to the detection region, a light receiving element provided at a position shifted from an optical path of the inspection light of the light emitting element by being faced with the detection region and receiving diffused light which is the inspection light having hit the smoke and diffused, so as to detect the smoke, and a reflecting member provided in the housing and deflecting and reflecting the inspection light emitted from the light emitting element so as not to enter the light receiving element.

Effect of the Invention

According to the present invention, smoke can be detected with high accuracy.

BRIEF DESCRIPTION OF THE DRAWINGS

FIG. 9 is a table showing an experiment result according to an example of the present invention.

Figure 1:
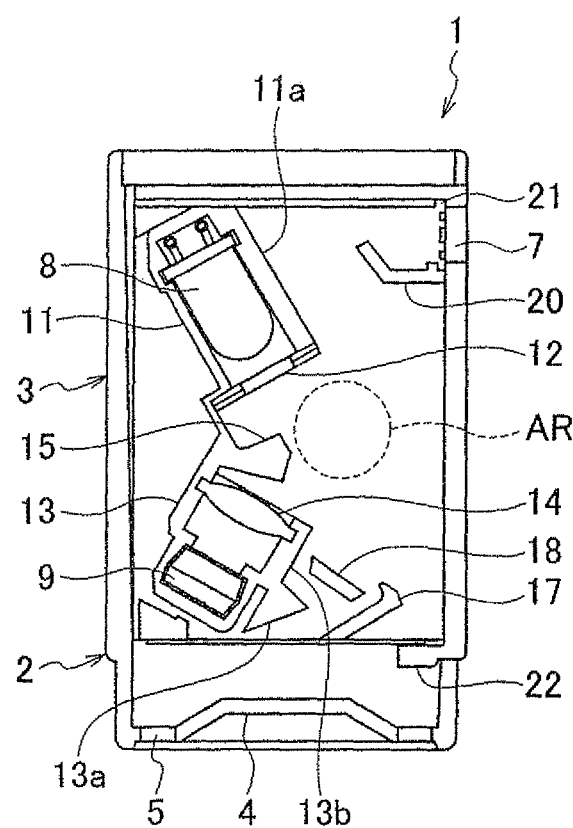
FIG. 1 is a side sectional view showing a prior-art photoelectric smoke sensor.

EXPLANATIONS OF REFERENCE NUMERALS 3 flat box portion
3a housing
3b detection-region side inner wall
3c side wall surface
3d side wall surface
8 light emitting element
9 direct light receiving element
17 labyrinth piece
25 protruding portion
31 photoelectric smoke sensor
32, 33 reflecting member
32a, 33a reflecting surface
41 light emitting element
42 light receiving element
43 shielding plate
44 lens
45 light receiving element accommodation portion
47 reflecting member
47a reflecting surface
48 reflecting member
48a reflecting surface

BEST MODE FOR CARRYING OUT THE INVENTION

Embodiments of the present invention will be described below. The photoelectric smoke sensor of the present invention is a highly sensitive smoke sensor which can be installed in a place where people gather such as a general household, a public facility and the like, and in a semiconductor manufacturing device in a factory, a machine tool, a power distribution panel, an industrial controller, a device or the like in which a fire can break out.

(A) First Embodiment

Figure 2:
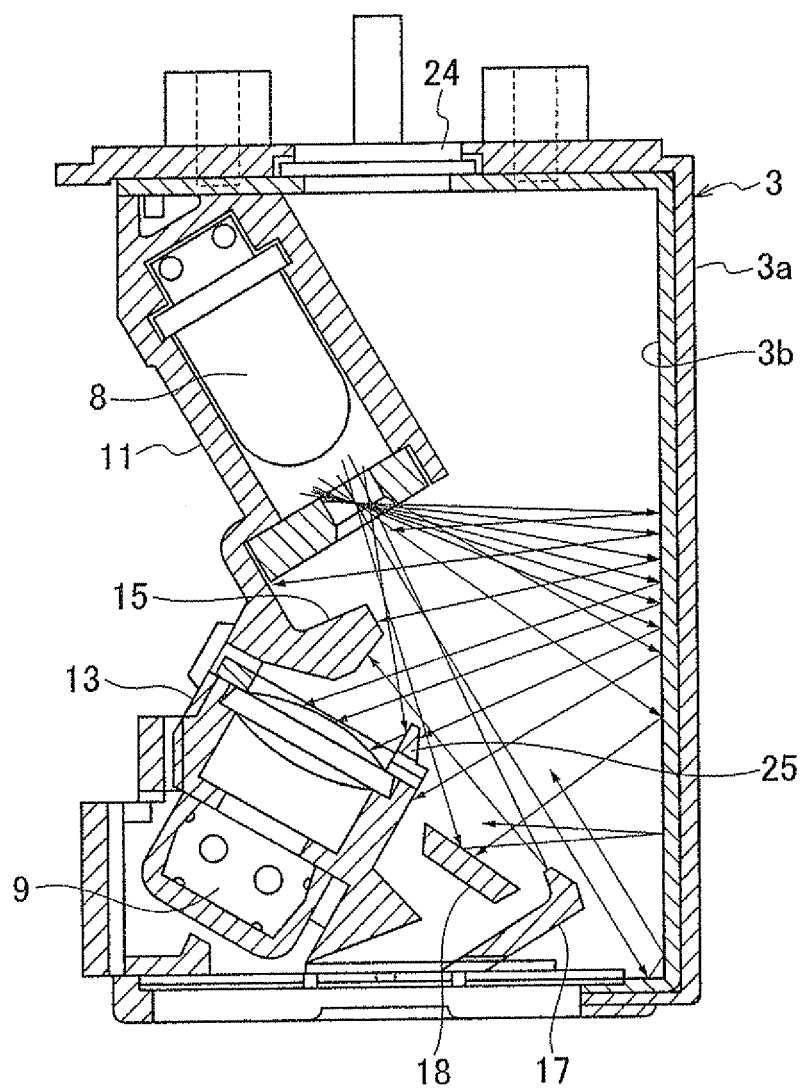
FIG. 2 is a side sectional view showing the prior-art photoelectric smoke sensor.

The photoelectric smoke sensor according to this embodiment is characterized in that a reflecting member is provided. For an explanation of the reflecting member while making a comparison with the prior-art technology, an explanation of the prior-art photoelectric smoke sensor, having generally the same configuration as that of the present invention, will be given first with reference to FIG. 2, and then an explanation of the photoelectric smoke sensor of this embodiment will be given with reference to FIG. 3. The prior-art photoelectric smoke sensor of FIG. 2 is the basis for the photoelectric smoke sensor of the present invention. The present invention is an improvement of the photoelectric smoke sensor of FIG. 2. Although an optical path of inspection light emitted from a light emitting element 8 in the photoelectric smoke sensor according to this embodiment is different from the one in FIG. 2, the optical path of the inspection light is left as it is in FIG. 3, in order to show that the reflecting member of the present invention is provided in the photoelectric smoke sensor having the configuration of FIG. 2.

The photoelectric smoke sensor in FIG. 2 generally has the configuration that is substantially the same as that of the above-described photoelectric smoke sensor of FIG. 1. The photoelectric smoke sensor of FIG. 2 is different from the photoelectric smoke sensor of FIG. 1 mainly in that a cylinder portion 2, a side-face small hole 7, a labyrinth piece 20, and an insect screen 21 are present or not. The rest of the configuration is the same as that of the photoelectric smoke sensor of FIG. 1. Thus, the same reference numerals are given to the same members and the description thereof will be omitted. The photoelectric smoke sensor of FIG. 2 has a small hole 24 provided in its top surface, instead of the side-face small hole 7. Moreover, if the photoelectric smoke sensor is specifically installed, there are other necessary configurations in addition to the configuration described in this embodiment, but since they are all known configurations, they are omitted here.

With the photoelectric smoke sensor having the configuration of FIG. 2, the inspection light emitted from a light emitting element 8 is reflected by a detection-region side inner wall 3b of a housing 3a of a flat box portion 3, and a part of the reflected light directly enters a light receiving element 9, as shown by arrows in FIG. 2. In addition, the reflected light reflected by a protruding portion 25 that is provided at an opening of the light receiving element 9 and by a protruding portion 17a of a labyrinth piece 17 may enter the light receiving element 9. Such light becomes noise and deteriorates inspection accuracy in the photoelectric smoke sensor.

Figure 3:
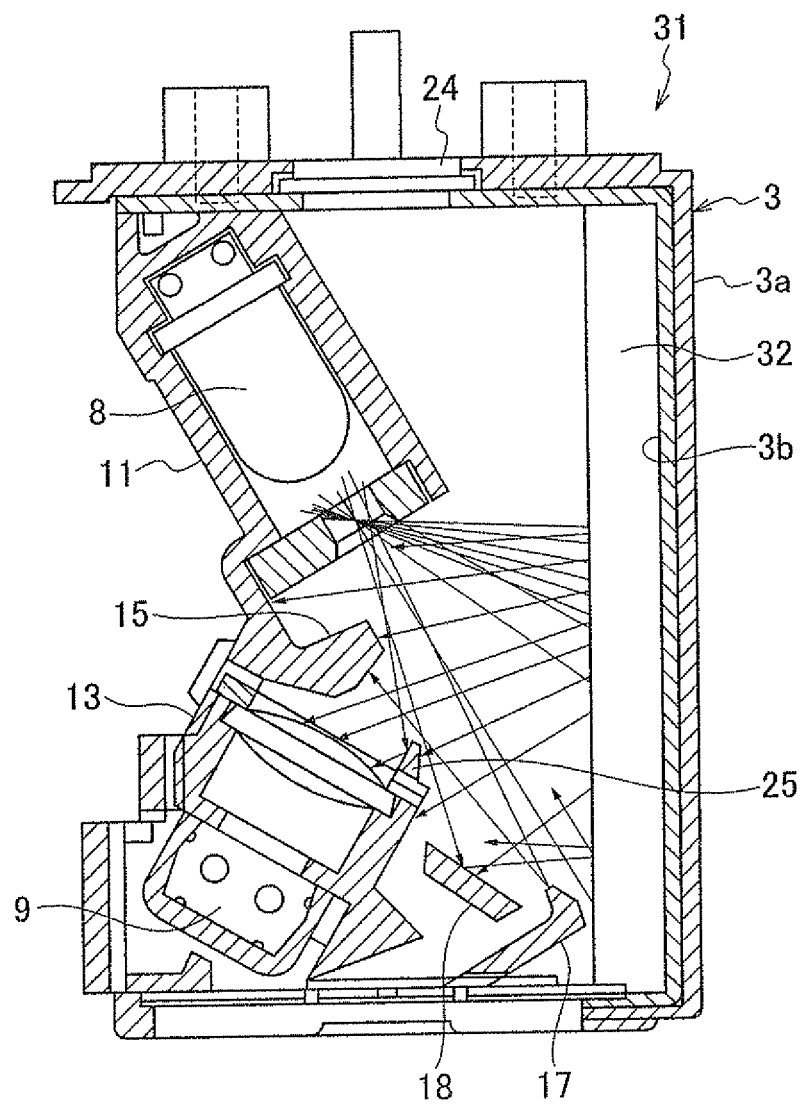
FIG. 3 is a side sectional view showing a photoelectric smoke sensor according to a first embodiment of the present invention.
Figure 4:
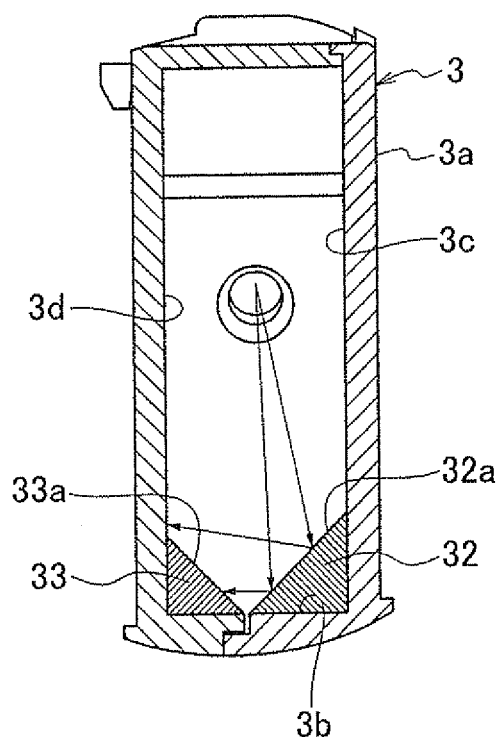
FIG. 4 is a plan sectional view of FIG. 3.

The photoelectric smoke sensor according to this embodiment is to control the reflected light entering the light receiving element 9 (the reflected light of the inspection light emitted from the light emitting element 8). In other words, the photoelectric smoke sensor according to this embodiment controls the reflected light that is mainly reflected by the detection-region side inner wall 3b. Specifically, reflecting members 32 and 33 are provided in a photoelectric smoke sensor 31, as shown in FIGS. 3 and 4. These reflecting members 32 and 33 are members deflecting inspection light emitted from the light emitting element 8 from the light receiving element 9 and to reflect the light so that the inspection light does not enter the light receiving element 9. The reflecting members 32 and 33 are provided on the detection-region side inner wall 3b of the housing 3a at positions opposite to the light emitting element 8 with the detection region AR (refer to FIG. 1) between them. The reflecting members 32 and 33 are provided on the whole region in the vertical direction of the detection-region side inner wall 3b as shown in FIG. 3. Further, the reflecting members 32 and 33 are provided with reflecting surfaces 32a and 33a, each being inclined having a V-shaped planar shape, as shown in FIG. 4. These reflecting surfaces 32a and 33a are surfaces deflecting the inspection light emitted from the light emitting element 8 from the light receiving element 9 in a direction not directed toward the light receiving element 9 and to reflect the light. The reflecting surface 32a is formed larger than the reflecting surface 33a. The reflecting surface 32a is provided on one side wall surface 3c side of the housing 3a and occupies a wider area. The reflecting surface 33a is provided on the other side wall surface 3d side of the housing 3a and occupies an area smaller than the reflecting surface 32a. As a result, the inspection light emitted from the light emitting element 8 is reflected irregularly by the two reflecting surfaces 32a and 33a. By reflecting the inspection light irregularly by the two reflecting surfaces 32a and 33a, the reflected light is reflected in a direction not directed toward the light receiving element 9 (deflected from the light receiving element 9) as shown in FIG. 4. Areas and inclination angles of the two reflecting surfaces 32a and 33a are set so that the reflected light is not directed toward the light receiving element 9 in relation with the light emitting element 8.

Some light in the reflected light is reflected twice by the V-shaped reflecting surfaces 32a and 33a and thus changing the direction by 180 degrees. However, if the inspection light is reflected twice, brightness is drastically attenuated, and a light amount is drastically decreased. Therefore, even if the reflected light reflected twice (secondary reflected light) enters the light receiving element 9, it becomes extremely weak light and does not cause a problem.

Moreover, the portions other than the above-described configuration are not particularly limited. The configuration that can be incorporated in the photoelectric smoke sensor of the present invention (peripheral configuration of the existing photoelectric smoke sensor) can be all applied to the present invention.

The photoelectric smoke sensor configured as above operates as follows.

The inspection light emitted from the light emitting element 8 toward the detection region AR is transmitted through the detection region AR and irradiates the reflecting members 32 and 33. Moreover, there is also the inspection light irradiating the side wall surfaces 3c and 3d, but this light is reflected by the side wall surfaces 3c and 3d and irradiates the reflecting members 32 and 33.

In the reflecting members 32 and 33, the light is irregularly reflected by the V-shaped reflecting surfaces 32a and 33a so as to eliminate the reflected light toward the light receiving element 9. A part of the reflected light goes toward the light receiving element 9, but such light has been reflected twice or more as described above and drastically attenuated, thus not causing any problem.

The reflected light reflected by the reflecting surfaces 32a and 33a irradiates the opposite reflecting surfaces 33a and 32a or the side wall surfaces 3e or 3d. Most of the reflected light reflected by the reflecting surfaces 33a and 32a irradiates the side wall surfaces 3c and 3d and is reflected by these side wall surfaces 3c and 3d. Moreover, most of the reflected light reflected by the side wall surfaces 3c and 3d irradiates the opposite side wall surfaces 3c and 3d and is reflected again. As a result, the reflected light of the inspection light gathers around the detection region AR and repeats reflection and rarely enters the light receiving element 9.

If smoke intrudes from the outside and reaches the vicinity of the detection region AR in this state, the inspection light from the light emitting element 8 hits the smoke and is diffused, the diffused light enters the light receiving element 9, and the smoke is detected. At this time, since the reflected light is distributed also around the detection region AR, the diffused light is also generated in this portion, thereby increasing the diffused light in the housing 3a of the flat box portion 3.

As a result, entry of the reflected light which becomes noise into the light receiving element 9 can be drastically decreased, and the diffused light by the smoke can be increased. Thus, the light receiving element 9 can detect the smoke with higher accuracy.

As a result of this, it is possible to keep the equipment as small as the prior-art photoelectric smoke sensor, and to detect the smoke with higher accuracy.

(B) Second Embodiment

Next, a second embodiment of the present invention will be explained.

Figure 5:
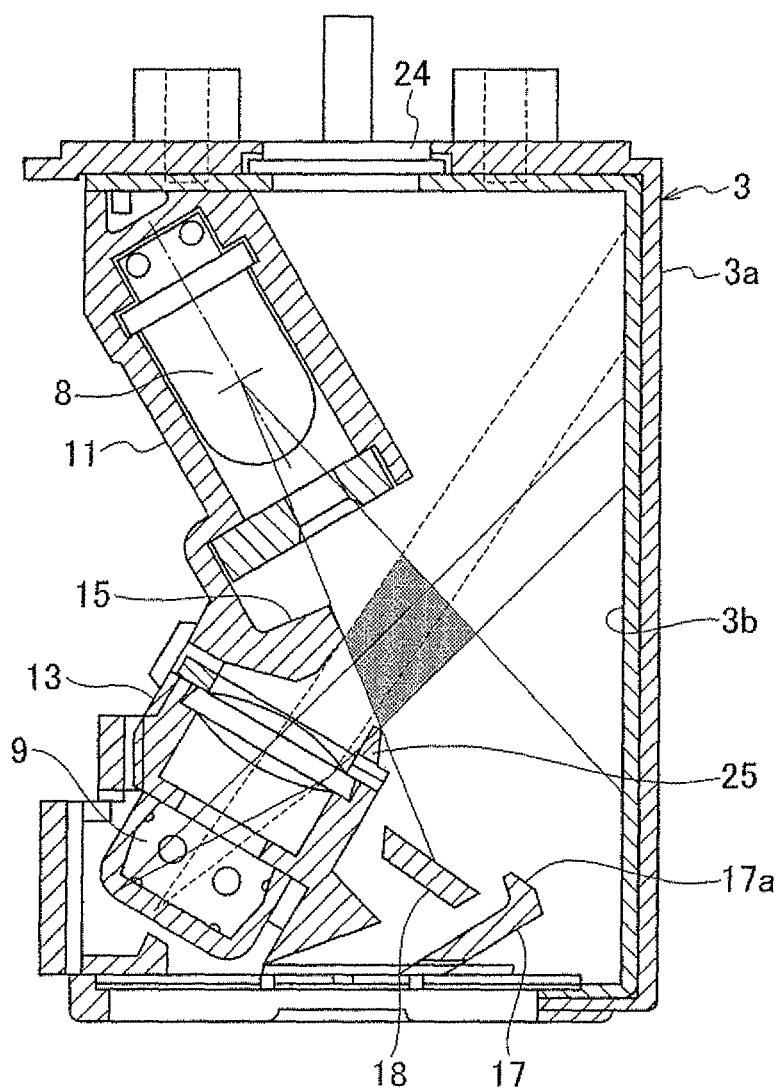
FIG. 5 is a side sectional view showing the prior-art photoelectric smoke sensor.
Figure 6:
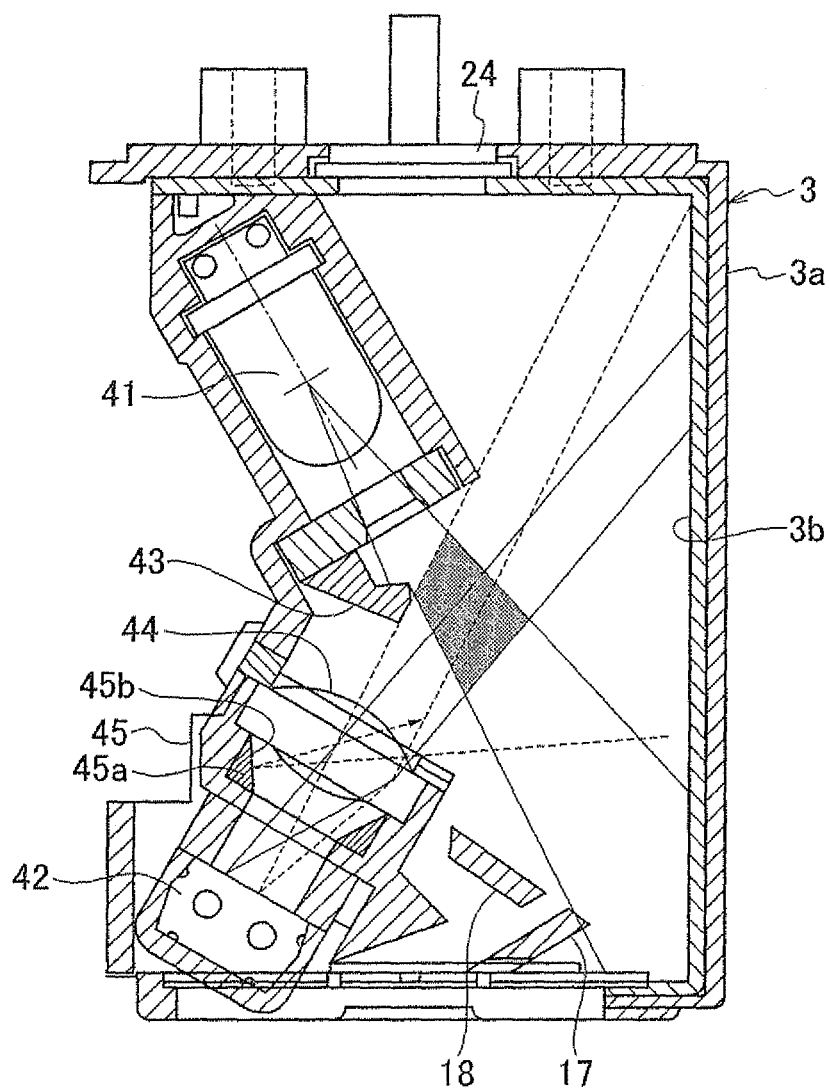
FIG. 6 is a side sectional view showing a photoelectric smoke sensor according to a second embodiment of the present invention.

According to this embodiment, the light source, the shielding plate, and the protruding portion such as the labyrinth in the photoelectric smoke sensor of FIG. 2 are improved. Incidentally, FIG. 5 is a view showing the state in which an inspection light irradiation angle of the light emitting element 8 and a viewing angle of the light receiving element 9 are overlapped with one another, in the prior-art photoelectric smoke sensor provided with the light emitting element 8, the light receiving element 9, and the shielding plate 15. FIG. 6 is a view showing the state in which an inspection light irradiation angle of a light emitting element 41 and a viewing angle of a light receiving element 42 are overlapped with one another, in the photoelectric smoke sensor according to this embodiment that is provided with the light emitting element 41, the light receiving element 42, and a shielding plate 43.

Figure 7:
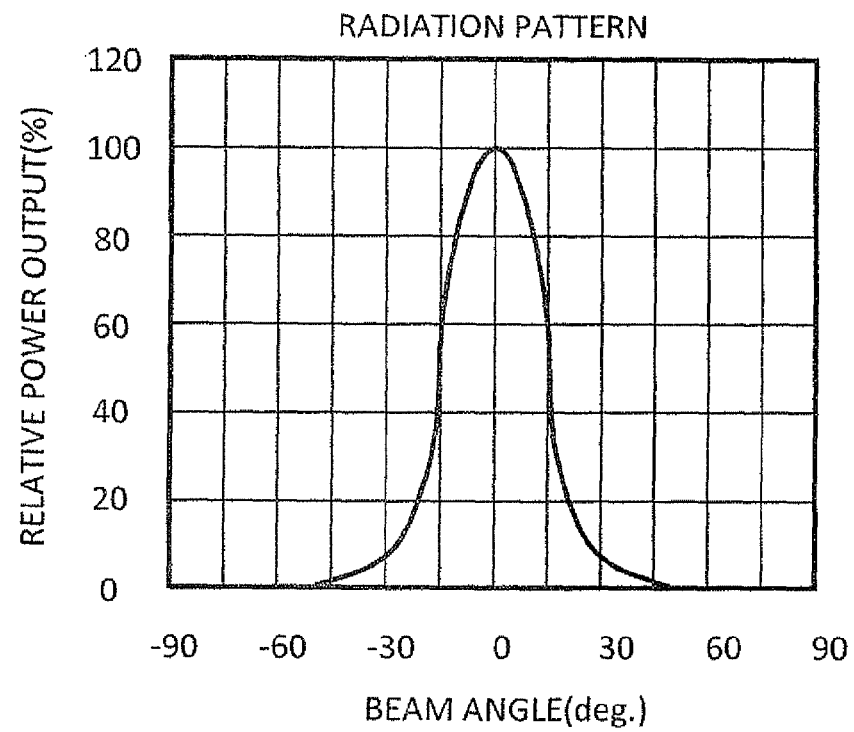
FIG. 7 is a graph showing a characteristic of a light source of a light emitting element of the prior-art photoelectric smoke sensor.
Figure 8:
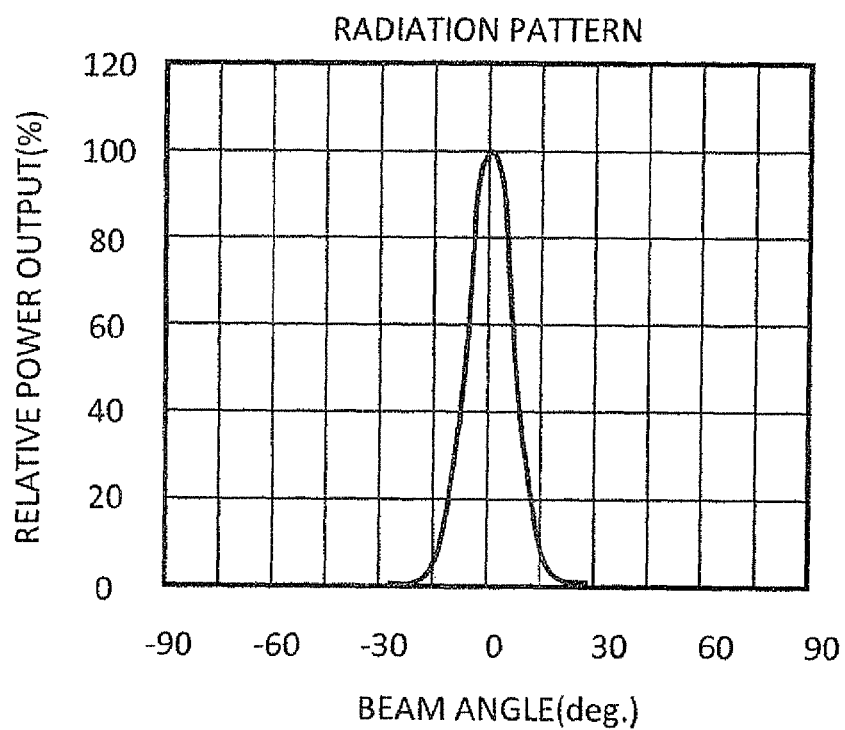
FIG. 8 is a graph showing a characteristic of a light source of a light emitting element of the photoelectric smoke sensor according to the second embodiment of the present invention.

According to this embodiment, a light amount of a light source of the light emitting element 41 is increased. In addition, directivity of the light source is increased. The inspection light emitting angle is narrowed. Specifically, the directivity is increased and the light is narrowed as in FIG. 8, as compared with the prior-art light source of FIG. 7. In other words, the inspection light is narrower and stronger than the prior-art inspection light.

The shielding plate 43 is a member that is provided between the light emitting element 41 and the light receiving element 42 and prevents the inspection light from the light emitting element 41 from directly entering the light receiving element 42.

The shielding plate 43 is provided on the light emitting element 41 side, at the position that is closer to the light emitting element 41 side, and is separated from the light receiving element 42.

The light receiving element 42 is configured in such a manner that the focal length of its lens 44 is shortened, the total length of a light receiving element accommodation portion 45 is reduced, and the light receiving element 42 is separated from the shielding plate 43. This extends space in front of the light receiving element 42, and widens a light entering angle. The light entering angle is an angle at which the light can enter, that is, an entering angle of the diffused light that enters from the inside of the housing 3a of the flat box portion 3 into the light receiving element 42. By widening the light entering angle, a diffused light amount to be taken into the light receiving element 42, namely, a signal is increased.

Inside the lens 44 in the light receiving element accommodation portion 45, an inclination member 45a is provided. The inclination member 45a is arranged to cover the peripheral edge portion of the lens 44 from its inside. On the surface of the inclination member 45a, an inclined surface 45b having a conical shape (tapered shape) is provided. This inclined surface 45b is a reflecting surface that reflects the reflected light entering the light receiving element accommodation portion 45 to the outside of the light receiving element accommodation portion 45. When the inspection light from the light emitting element 41 is reflected in the housing 3a, the reflected light is shielded for the most part by the shielding plate 43 and the like. However, a part of the reflected light may enter the light receiving element accommodation portion 45. Such reflected light often enters in the vicinity of the lens 44. Therefore, the inclined surface 45b provided in the vicinity of the lens 44 allows the reflected light entering the light receiving element accommodation portion 45 to be reflected to the outside, and prevents it from entering the light receiving element 42. Incidentally, the inclined surface 45b, which needs to reflect light, may be formed as a mirror surface for the effective reflection.

Further, the protruding portion 17a of the labyrinth piece 17 and the protruding portion 25 at the opening of the light receiving element 42, as shown in FIG. 5, are omitted. This is because the protruding portions 17a and 25 may reflect the inspection light and allow the inspection light to enter the light receiving element 42.

When the smoke flows into the detection region AR (refer to FIG. 1) in the photoelectric smoke sensor configured as above, the inspection light, as the strong light, hits against the smoke and produces the diffused light. The diffused light becomes the strong light in proportion to the inspection light, and enters the light receiving element 42.

As the light receiving element 42 has the wider light entering angle, it takes in a larger amount of the diffused light and detects the smoke.

As a result, entry of the reflected light which becomes noise into the light receiving element 42 can be drastically decreased, and the diffused light entering the light receiving element 42 can be increased. Thus, the smoke can be detected with higher accuracy.

As a result of this, it is possible to keep the equipment as small as the prior-art photoelectric smoke sensor, and to detect the smoke with higher accuracy.

(C) Example

Subsequently, an experiment result using the photoelectric smoke sensor, in which all the features of the above-described first embodiment and the second embodiment are combined, will be described in comparison with the prior-art photoelectric smoke sensor.

As the light emitting element 41 of the photoelectric smoke sensor in this example, an element with the following performances was used. That is, a light emitting element having an output of 11 mW, an applied voltage of 9 V, and an applied current of 550 mA was used.

Moreover, as a light emitting element of the prior-art photoelectric smoke sensor, a light emitting element having an output of 11 mW, an applied voltage of 9 V, and an applied current of 300 mA was used. As a result, the light emitting element 41 of this example has a light amount increased from that of the prior-art light emitting element.

Moreover, as the light receiving element 42 of the photoelectric smoke sensor of this example, an element provided with the performances discussed below was used. That is, a light receiving element having performances such that a peak sensitivity wavelength is 940 nm, a color temperature is 2856 K, an open voltage when an EV display value of a standard tungsten bulb is at 1000 Lx is 0.35 V, and a short-circuit current is 75 μA was used.

As the light receiving element of the prior-art photoelectric smoke sensor, a light receiving element similar to the light receiving element 42 of the above-described example was also used.

By using these photoelectric smoke sensors, a smoke experiment was conducted at the detection concentration of 5%/m. The result of this experiment is shown in Table in FIG. 9. Here, three types of the photoelectric smoke sensors, that is, the prior-art photoelectric smoke sensor, a photoelectric smoke sensor in which the prior-art light emitting element and the light receiving element are attached to the flat box portion 3 provided with the reflecting members 32 and 33 of the present invention, and the photoelectric smoke sensor of this example were used in the experiment.

In Table in FIG. 9, ADL at 108 in the prior-art photoelectric smoke sensor was decreased to 13 in the prior-art photoelectric smoke sensor using the flat box portion 3 of the present invention. The value was 25 in the photoelectric smoke sensor of this example, which indicates drastic reduction from the prior-art photoelectric smoke sensor. That is, the value was reduced to 13 in the prior-art photoelectric smoke sensor using the flat box portion 3 of the present invention, and a light amount of the light emitting element 41 of this example could be increased. As a result, in the photoelectric smoke sensor of this example, the ADL could be drastically decreased as compared with the prior-art photoelectric smoke sensor.

Moreover, ADH at 147 in the prior-art photoelectric smoke sensor was decreased to 90 in the prior-art photoelectric smoke sensor using the flat box portion 3 of the present invention. The value was 109 in the photoelectric smoke sensor of this example. As a result, no significant change of signal was found.

As a result, the ADH-ADL rose from 39 in the prior-art photoelectric smoke sensor to 77 in the prior-art photoelectric smoke sensor using the flat box portion 3 of the present invention. In the photoelectric smoke sensor of this example, the value was 84. If the value is converted to an amount of change of 1%/m, the value at 7.8 in the prior-art photoelectric smoke sensor rose to 15.4 in the prior-art photoelectric smoke sensor using the flat box portion 3 of the present invention. The value was 17 in the photoelectric smoke sensor of this example. As a result, the amount of change was increased to be almost twice as large as the prior-art product. Furthermore, S/N ratio at 0.37 in the prior-art photoelectric smoke sensor rose to 5.93 in the prior-art photoelectric smoke sensor using the flat box portion 3 of the present invention. The value was 3.3 in the photoelectric smoke sensor of this example. As a result, in the photoelectric smoke sensor of this example, noise resistance was drastically improved as compared with the prior-art photoelectric smoke sensor.

As a result, the prior-art photoelectric smoke sensor using the flat box portion 3 of the present invention senses smoke at sensitivity higher than that of the prior-art photoelectric smoke sensor, and it is known that the photoelectric smoke sensor of this example senses smoke at higher sensitivity. The photoelectric smoke sensor of this example particularly has an ADH-ADL value much higher than that of the prior-art photoelectric smoke sensor using the flat box portion 3 of the present invention, and it is known that the smoke is sensed with high accuracy.

As a result, the photoelectric smoke sensor of this example can sense smoke at high sensitivity.

(D) Variation

Although the features, such as the reflecting members 32 and 33, are provided in the invention according to the above-described embodiments and the like, the invention is not limited to the three aspects, that is, the first embodiment, the second embodiment, and the example in which the first embodiment and the second embodiment are combined, and other combinations may be employed. Either one or two or more features, constituting the invention and described in the above-described embodiments, may be combined as necessary so as to form a photoelectric smoke sensor. In this case, too, the actions and effects similar to those in the above-described embodiments can be exerted.

Figure 10:
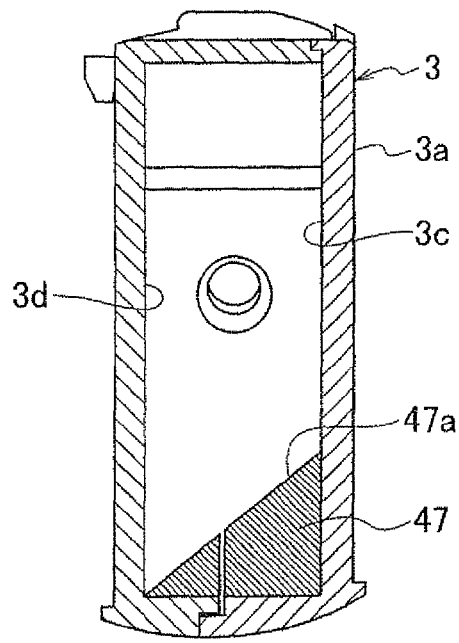
FIG. 10 is a plan sectional view of the photoelectric smoke sensor according to a first variation of the present invention.

In the above-described first embodiment, the V-shaped reflecting surfaces 32a and 33a are provided by the reflecting members 32 and 33, but as shown in FIG. 10, one reflecting surface 47a can be provided by one large reflecting member 47. As a result, the inspection light is reflected by the reflecting surface 47a and all irradiates the side wall surface 3d and is reflected by this side wall surface 3d. Then, secondary reflected light is drastically attenuated. Therefore, the inspection light from the light emitting element can be reflected in a direction not directed to the light receiving element. In this case, too, the actions and effects similar to those in the first embodiment can be exerted.

Figure 11:
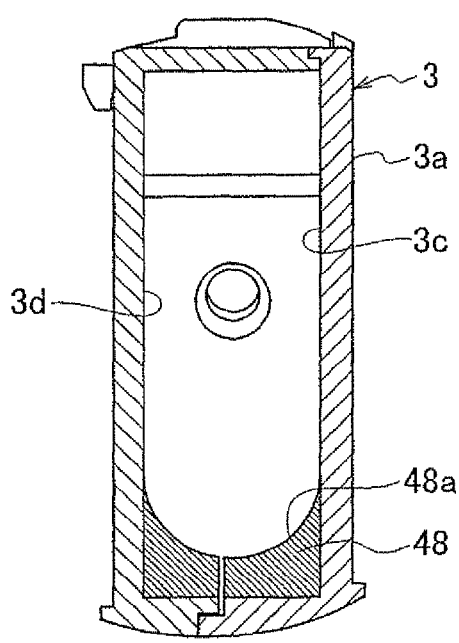
FIG. 11 is a plan sectional view of the photoelectric smoke sensor according to a second variation of the present invention.

Moreover, as shown in FIG. 11, a curved reflecting surface 48a may be provided by the reflecting member 48. Furthermore, the reflecting surface 48a may be formed so that the reflected light gathers in the detection region AR and its periphery like a concave mirror of a reflecting telescope. This reflecting surface 48a allows the inspection light from the light emitting element to be reflected in the direction gathering to the detection region. That is, the reflecting surface 48a may be configured to be curved so that the inspection light and the reflected light gather in the detection region AR and its periphery and more diffused light by the smoke flowing into the housing 3a can be generated. In this case, the reflecting surface 48a may be formed as a mirror surface. By forming the reflecting surface 48a as a mirror surface, more reflected light can be gathered to the detection region AR and its periphery.

By these configurations, smoke can be detected with higher accuracy.

The invention claimed is:

1. A photoelectric smoke sensor which detects smoke flowing into a housing by light, comprising:
    a light emitter provided by being faced with a detection region in the housing and emitting inspection light to the detection region;
    a light receiver provided at a position shifted from an optical path of the inspection light of the light emitter by being faced with the detection region and receiving diffused light which is the inspection light having hit the smoke and diffused, so as to detect the smoke; and
    first and second reflecting members provided in the housing and deflecting and reflecting the inspection light emitted from the light emitter so as not to enter the light receiver,
    wherein the first and second reflecting members extend on two sides of the detection region along an entire vertical extent of a first inner wall of the housing that is opposite the light emitter, the first and second reflecting members each having a respective inclined planar reflecting surface to reflect light emitted from the light emitter back to the detection region in a direction that is not directed to the light receiver, and
    wherein planes of the respective inclined planar reflecting surfaces intersect at an angle to form a V-shape in a horizontal cross-section of the photoelectric smoke sensor.

2. The photoelectric smoke sensor according to claim 1, wherein
    a light amount and directivity of a light source of the light emitter is inversely related to an inspection light emitting angle.

3. The photoelectric smoke sensor according to claim 1,
    a light entering angle of the light receiving element is determined by a distance between a shielding plate and the light emitter, the shielding plate being provided between the light emitter and the light receiver to prevent the inspection light from the light emitter from directly entering the light receiver, and wherein a separation distance of the shielding plate from a side of the light receiver is determined by a focal length of a lens of the light receiver.

4. The photoelectric smoke sensor according to claim 1, wherein
   a labyrinth that avoids intrusion of ambient light and allows intrusion of smoke is provided in the housing.

5. The photoelectric smoke sensor according to claim 1, wherein
   the light receiver and a lens are attached in a light receiver accommodation portion, and an inclination member is arranged to cover the peripheral edge of the lens in the light receiver accommodation portion, and
   the inclination member is provided with an inclined surface that reflects reflected light, entering into a peripheral portion of the lens in the light receiver accommodation portion, to an outer side of the light receiver accommodation portion.

6. The photoelectric smoke sensor according to claim 1, wherein
   one of the first and second reflecting members reflects the inspection light emitted from the light emitter to the other of the first and second reflecting members or a second inner wall of the housing, and
   the other of the first and second reflecting members reflects the light from the one of the first and second reflecting members back to the detecting region.

\* \* \* \* \*